United States Patent [19]
Schmieding

[11] Patent Number: 5,425,733
[45] Date of Patent: * Jun. 20, 1995

[54] INTERFERENCE SCREW WITH ROUNDED BACK END AND CANNULATED SHEATH FOR ENDOSTEAL FIXATION OF LIGAMENTS

[75] Inventor: Reinhold Schmieding, Naples, Fla.

[73] Assignee: Arthrex, Inc., Naples, Fla.

[*] Notice: The portion of the term of this patent subsequent to May 18, 2010 has been disclaimed.

[21] Appl. No.: 70,967

[22] Filed: Jun. 4, 1993

Related U.S. Application Data

[63] Continuation-in-part of Ser. No. 19,357, Feb. 18, 1993, which is a continuation-in-part of Ser. No. 836,721, Feb. 19, 1992, Pat. No. 5,211,647.

[51] Int. Cl.$^6$ .............................................. A61B 17/58
[52] U.S. Cl. ........................................ 606/104; 606/73; 606/96; 606/86
[58] Field of Search ................. 606/88, 73, 86, 96, 606/97, 98, 72, 104; 411/393, 395, 414, 307, 408, 403, 404, 426

[56] References Cited

U.S. PATENT DOCUMENTS

| | | | |
|---|---|---|---|
| 2,295,314 | 5/1940 | Whitney | 411/393 |
| 2,414,882 | 9/1943 | Longfellow | 606/73 |
| 2,570,465 | 10/1951 | Lundholm | 606/65 |
| 4,259,072 | 3/1981 | Hirabayashi et al. | 433/173 |
| 4,450,834 | 5/1984 | Fischer | 606/80 |
| 4,450,835 | 5/1984 | Asnis et al. | 606/73 |
| 4,467,478 | 8/1984 | Jurgutis | 623/13 |
| 4,537,185 | 8/1985 | Stednitz | 606/73 |
| 4,590,928 | 5/1986 | Hunt et al. | 606/72 |
| 4,597,766 | 7/1986 | Hilal et al. | 623/13 |
| 4,605,414 | 8/1986 | Czajka | 623/13 |
| 4,632,100 | 12/1986 | Somers et al. | 606/73 |
| 4,668,233 | 5/1987 | Seedhom et al. | 623/13 |
| 4,712,542 | 12/1987 | Daniel et al. | 606/96 |
| 4,716,893 | 1/1988 | Fischer et al. | 606/66 |
| 4,738,255 | 4/1988 | Goble et al. | 606/86 |
| 4,784,126 | 11/1988 | Hourahane | 606/60 |
| 4,790,850 | 12/1988 | Dunn et al. | 623/13 |
| 4,828,562 | 5/1989 | Kenna | 623/13 |
| 4,870,957 | 10/1989 | Goble et al. | 606/73 |
| 4,872,451 | 10/1989 | Moore et al. | 606/72 |
| 4,927,421 | 5/1990 | Goble et al. | 606/73 |
| 4,950,270 | 8/1990 | Bowman | 606/73 |
| 4,961,421 | 10/1990 | Muller | 606/180 |
| 4,997,433 | 3/1991 | Goble et al. | 606/64 |
| 5,004,474 | 4/1991 | Fronk et al. | 623/13 |
| 5,169,400 | 12/1992 | Muhling | 606/73 |
| 5,211,647 | 5/1993 | Schmieding | 606/104 |

FOREIGN PATENT DOCUMENTS

| | | | |
|---|---|---|---|
| 317406 | 5/1989 | European Pat. Off. | 606/73 |
| 0440991 | 8/1991 | European Pat. Off. | |
| 3434807 | of 1986 | Germany | 606/73 |
| 9203980 | 3/1992 | WIPO | 606/73 |

OTHER PUBLICATIONS

M. Kurosaka et al. "A Biomechanical Comparison of Different Surgical Techniques of Graft Fixation in Anterior Cruciate Ligament Reconstruction," *Am. J. Sports Med.*, vol. 15, No. 3 (1987).

K. Lambert, "Vascularized Patellar Tendon Graft with Rigid Internal Fixation for Anterior Cruciate Ligament Insufficiency" *Clinical Orthopaedics and Related Research*, No. 172 (Jan.–Feb. 1983).

*Primary Examiner*—Robert A. Hafer
*Assistant Examiner*—David Kenealy
*Attorney, Agent, or Firm*—Ostrolenk, Faber, Gerb & Soffen

[57] ABSTRACT

An interference screw and sheath for endosteal fixation of ligaments. A graft, attached between previously cut bone blocks, is placed under tension in a graft tunnel. The screw is driven between the bone to which the graft is being fixed and a corresponding one of the bone blocks. The screw includes an end portion having rounded back edges for protecting the graft from inadvertent damage after the sheath has been removed. The screw may be cannulated for insertion over a prepositioned guide pin. The guide pin has a larger than normal diameter to prevent the pin from bending during insertion. The screw cannulation is sufficiently large to accommodate the enlarged guide pin. The sheath has a cutout at one end such that during screw insertion, the graft is covered by the sheath and protected from the threads of the screw, while the bone to which the graft is being fixed is exposed to the threads of the screw.

10 Claims, 5 Drawing Sheets

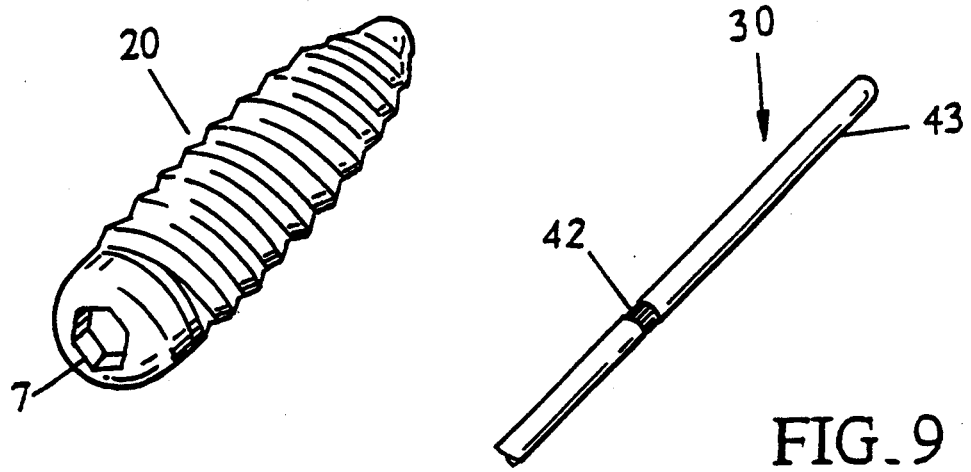
FIG. 7
FIG. 9
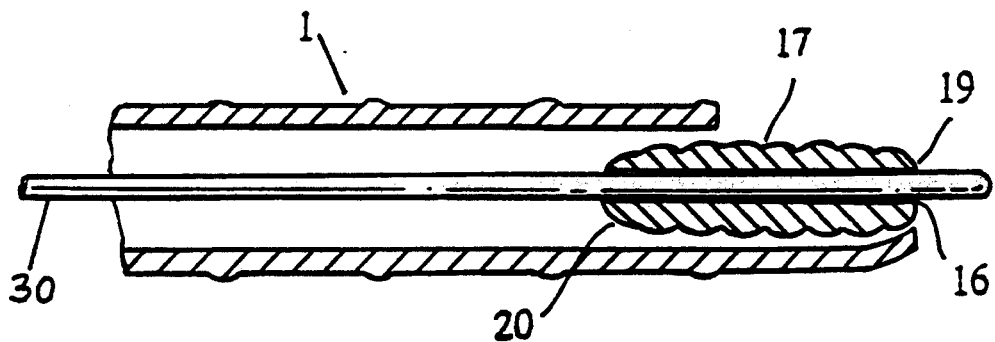
FIG. 8
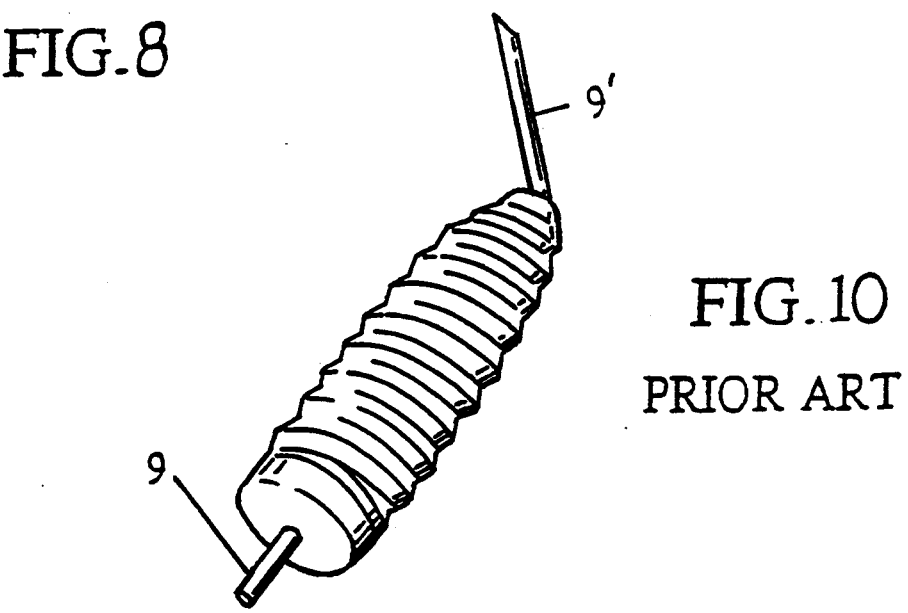
FIG. 10
PRIOR ART

INTERFERENCE SCREW WITH ROUNDED BACK END AND CANNULATED SHEATH FOR ENDOSTEAL FIXATION OF LIGAMENTS

This is a continuation-in-part of application Ser. No. 08/019,357, filed Feb. 18, 1993, which is a continuation-in-part of application Ser. No. 07/836,721, filed Feb. 19, 1992, now U.S. Pat. No. 5,211,647. The disclosures of these related applications are herein incorporated by reference.

BACKGROUND OF THE INVENTION

1. Field of the Invention

The present invention relates to an interference screw for endosteal fixation of a ligament and, more specifically, to an interference screw having a rounded back end and a larger than normal cannulation. The invention also relates to a cannulated sheath for an interference screw.

2. Description of the Related Art

When a ligament or tendon becomes detached from a bone, surgery is usually required to resecure the ligament or tendon. Often, a substitute ligament or graft is attached to the bone to facilitate regrowth and permanent attachment. Various methods of graft attachment are known, such as staples and sutures over buttons. However, such methods often do not provide a sufficiently strong attachment to withstand the normal tensile loads to which they are subjected.

A stronger graft attachment is obtained by using an interference screw to wedge a graft bone block to the wall of a graft tunnel formed through the bone. FIG. 1 illustrates this method, in which the graft 2, with bone blocks 4,6 at each end, is pulled through a graft tunnel 8 in the tibia 10, by applying a tensile force on sutures 12 attached to leading bone block 6. The leading bone block 6 is brought forward into the femur 14 until it is fully nested in a graft tunnel in the femur. Then, with tension applied to the graft 2 via sutures 12, a driver is used to insert interference screws 16 between the bone blocks 4,6 and the graft tunnel, first in the femur and then in the tibia, as shown in FIG. 2. Although interference screw attachment by the above-described method is more secure than using staples or the like, the graft can be inadvertently cut or frayed by the sharp edges of the interference screw during insertion and after fixation.

A thin guide pin is often used in conjunction with the interference screw to properly locate the screw against the bone block. Ideally, the screw, when fully nested, should be parallel to the graft. However, as shown in FIG. 10, during screw insertion with a thin guide pin, the thin pin tends to bend, allowing the screw to diverge off course and nest at an angle with respect to the bone block and the graft. Moreover, insertion of the guide pin is inaccurate, since the surgeon has to eye the correct depth of the insertion of the pin.

SUMMARY OF THE INVENTION

The present invention overcomes the above deficiencies by providing an interference screw configured with a rounded back end (i.e. no threads are present on the back end of the screw) to prevent inadvertent cutting or fraying of the graft by the screw during and after the screw has been inserted. The leading end of the screw is tapered while the back end has an inverse hex-head for receiving a hex-head screwdriver.

In one embodiment of the invention, the interference screw is cannulated, and a guide pin having a larger than normal diameter is used to guide the interference screw. The large diameter guide pin does not bend and thus gives the surgeon better control over the location of the screw during the fixation process. The interference screw is provided with a correspondingly enlarged cannulation and is guided by the guide pin to the proper position between the graft bone block and the bone.

An etched marking on the end of the guide pin assists the surgeon in gauging the correct depth of insertion of the pin. See parent application Ser. No. 08/019,357, assigned to the same assignee as the present application, and herein incorporated by reference.

The interference screw of the present invention is preferably made of titanium, although, other hard metals may be used, such as titanium allows, stainless steel and stainless steel alloys, and certain biodegradable materials specially tailored for hardness, tensile strength, and compressive strength.

The method of the present invention includes the steps of drilling a graft tunnel through adjacent bone masses, extending a substitute ligament with bone blocks in the graft tunnel under tension between the adjacent bone masses, inserting an interference screw with a rounded back end into the cannula of the sheath, and driving the interference screw between the tunnel wall and the bone block portion of the graft.

In another embodiment of the present invention, a guide pin having an enlarged diameter is inserted in the graft tunnel before positioning the interference screw. The interference screw is cannulated with an oversized cannulation and is guided by the guide pin during insertion and driving of the interference screw.

The present invention also achieves the foregoing objectives by providing a cylindrical cannulated sheath for protecting the ligament graft during insertion of an interference screw. The sheath is configured such that one end includes a cutout portion extending around up to one-half the circumference of the sheath, preferably one-third. The cutout enables the interference screw to be exposed to the tunnel wall of the bone during insertion, while at the same time covering the side of the screw facing the graft, thus protecting the graft from the screw threads during screw insertion. The sheath may optionally be provided with a thread-like continuous ridge on its outer surface to facilitate rotational insertion and removal of the sheath.

Other features and advantages of the present invention will become apparent from the following description of the invention which refers to the accompanying drawings.

BRIEF DESCRIPTION OF THE DRAWINGS

FIGS. 5 and 7 show the interference screw of the present invention.

FIG. 8 is a cross-section of the interference screw guide pin and cannulated sheath of the present invention.

FIG. 9 illustrates the guide pin of the present invention.

FIG. 10 illustrates a conventional guide pin bending during screw insertion.

DETAILED DESCRIPTION OF A PREFERRED EMBODIMENT

Figure 1:
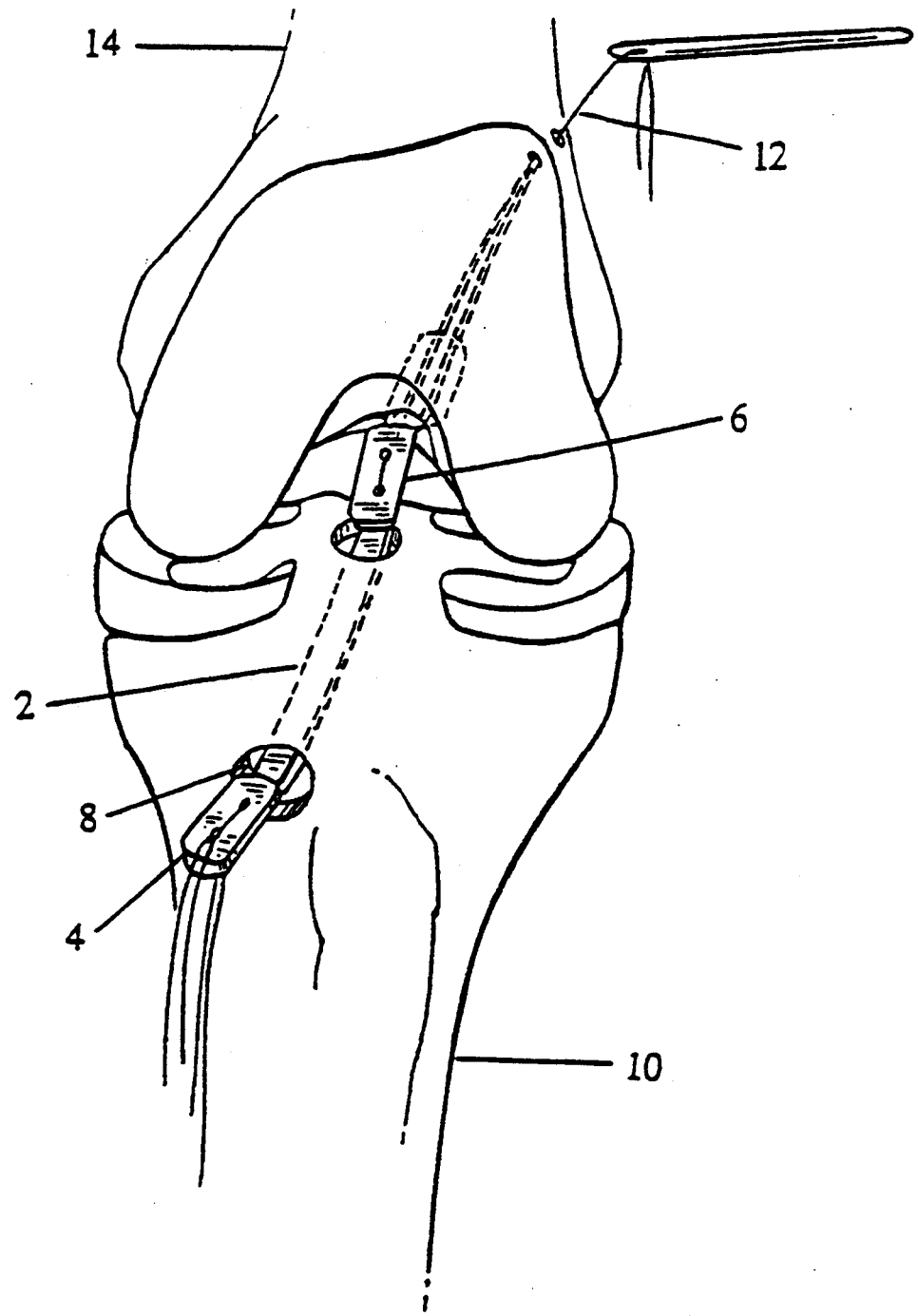
FIG. 1 shows a typical graft attached between two previously cut bone blocks being positioned in a graft tunnel.
Figure 2:
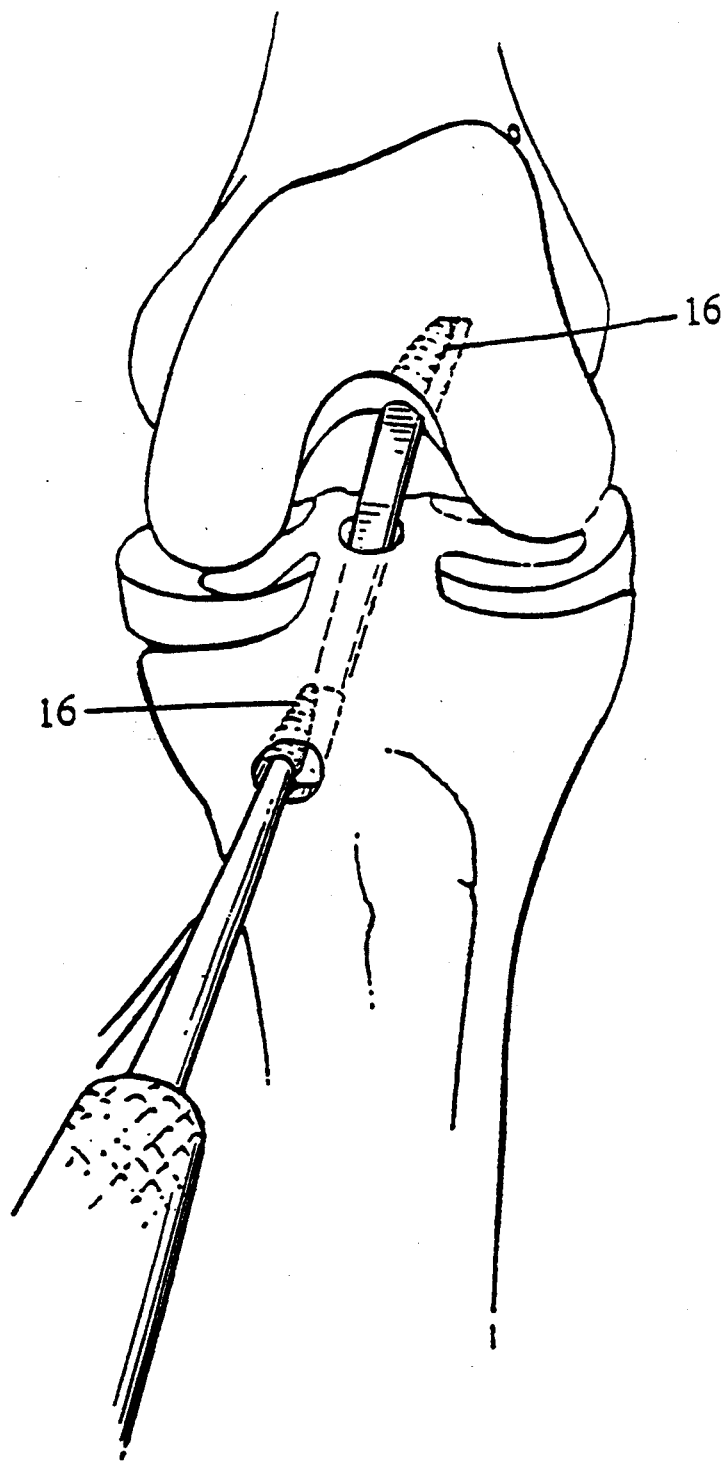
FIG. 2 shows interference screws driven between the bone masses and the corresponding bone blocks.
Figure 3:
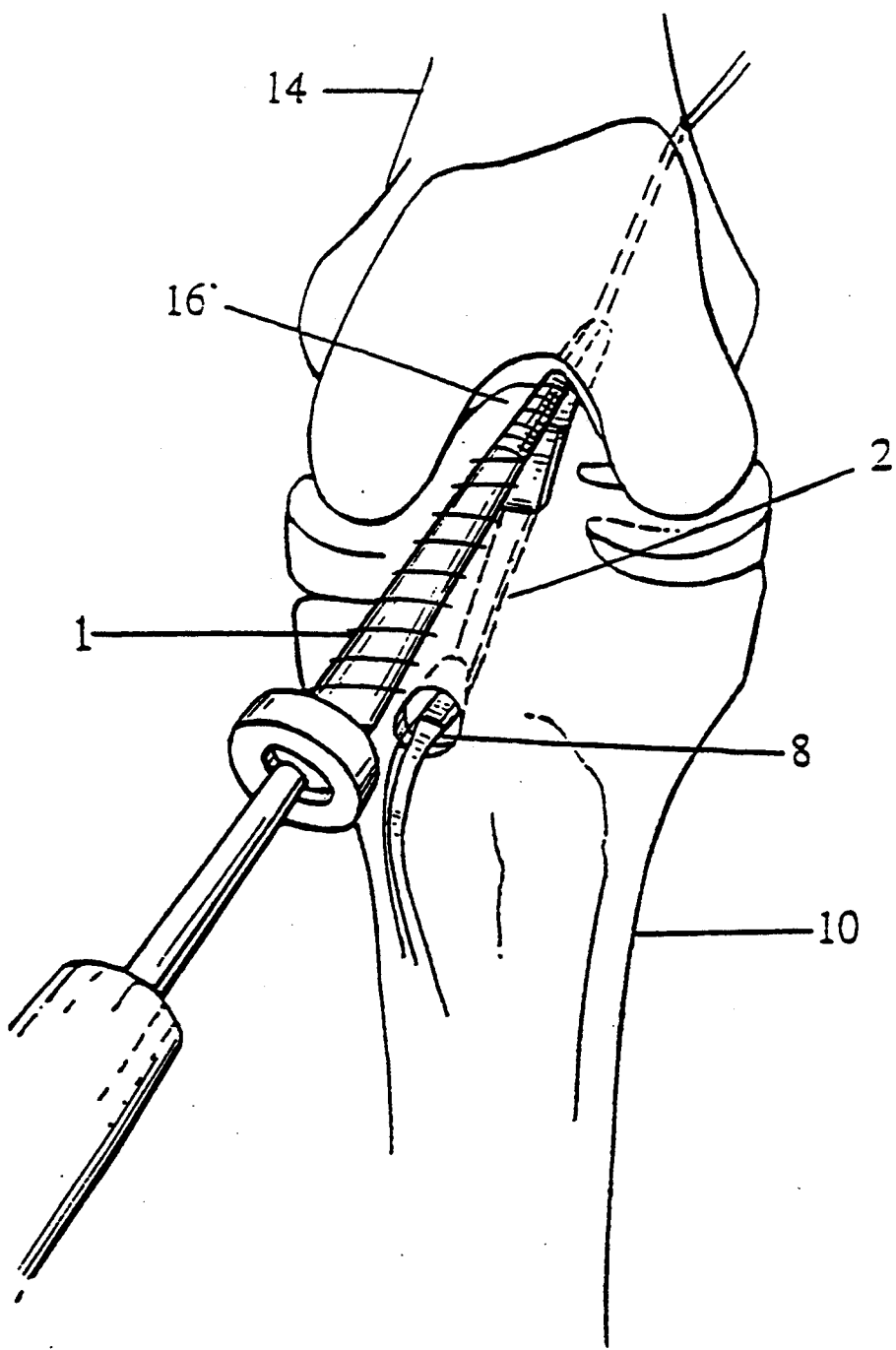
FIG. 3 shows the cannulated sheath being used to insert an interference screw in accordance with the method of the present invention.
Figure 4:
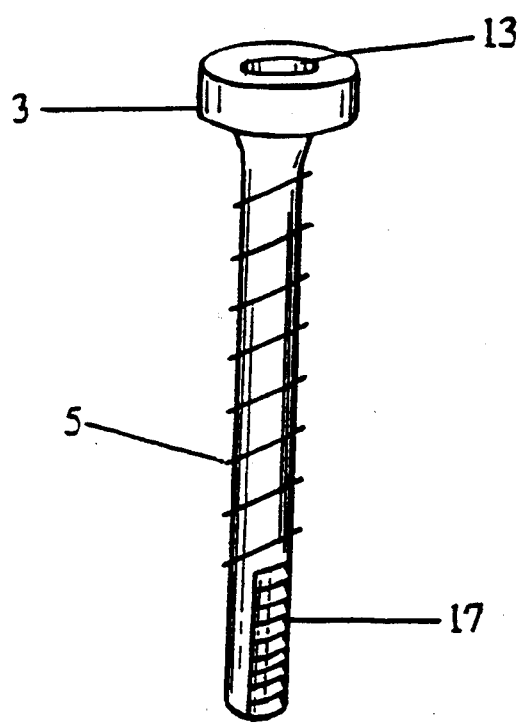
FIG. 4 shows the cannulated sheath of the present invention with the interference screw exposed by the cutout.

Referring to FIGS. 3 and 4, in the preferred embodiment, a cylindrical cannulated sheath 1 is preferably provided to receive an interference screw 16 for use during endosteal fixation of a substitute ligament or graft 2.

The sheath 1 has a head 3 at one end and a cutout 17 at the other. The cutout 17, which extends over up to one-half of the circumference (preferably one-third) of the cylindrical sheath 1, enables the interference screw to be driven into the bone mass or tibia 10, while at the same time protecting the graft from inadvertent damage such as fraying or cutting by the screw threads 19. The sheath preferably includes a continuous thread-like ridge 5 on its outer surface, which allows the sheath to be rotated in and out of position. The sheath is preferably made of plastic.

Figure 5:
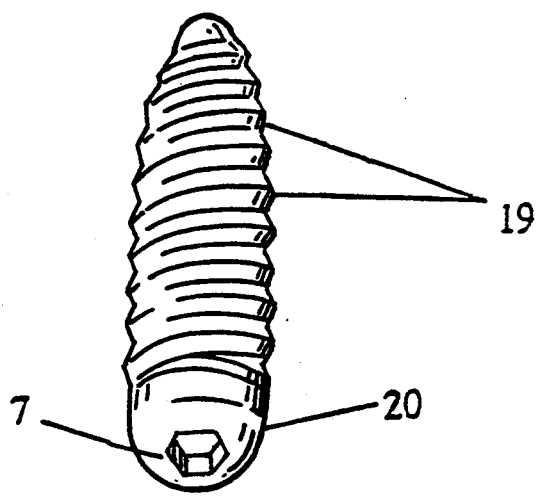

As shown in FIG. 5, the front end of the interference screw 16 is tapered, while the back end 20 is rounded in a semi-spherical shape and has a smooth surface without threads. The smooth surface of rounded back end 20 prevents inadvertent damage to the graft after fixation. Back end 20 preferably includes an inverse hex head 7 adapted to receive a hex head screwdriver.

The interference screw is preferably made of titanium, although, other hard metals may be used, such as titanium alloys, stainless steel alloys, and certain biodegradable materials specially tailored for hardness, tensile strength, and compressive strength.

Figure 6:
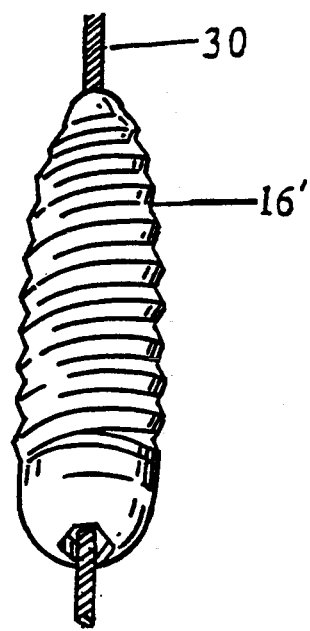
FIG. 6 shows a cannulated interference screw of an alternate embodiment of the present invention.

In an alternate embodiment as shown in FIG. 6, the interference screw 16' is cannulated for receiving a guide pin. The guide pin is positioned between the graft bone block and the femur 14 for guiding the sheath 1 and the cannulated screw 16' into position. A cannulated hex head screwdriver is used to drive the cannulated screw.

The method of the invention will now be described in conjunction with FIG. 3, it being understood that the use of a cannulated interference screw for endosteal fixation of a substitute ligament or graft is well known in the art. See, e.g., U.S. Pat. Nos. 4,927,421 and 4,950,270, the disclosures of which are herein incorporated by reference.

As is the usual practice in the art, a graft tunnel 8 is first drilled through the adjoining bones, in this case the tibia 10 and the femur 14. A graft 2, attached between previously cut bone blocks, preferably a patellar tendon, is extended under tension within the graft tunnel 8 between the tibia 10 and the femur 14. In the present invention, a guide pin is then hand positioned between the bone block 6 and the graft tunnel 8 adjacent the femur 14. The cannulated sheath 1 is placed over the guide pin and guided to a position such that the graft 2 is covered by the sheath 1, while the graft tunnel 8 in the femur 14 is exposed by the cutout 17. The cannulated interference screw 16' is then placed over the guide pin and inserted into the cannula 13 of the sheath.

The interference screw 16' is driven into the graft tunnel 8 between the femur 14 and the bone block 6. During screw insertion, the sheath 1 covers the graft 2, thus protecting the graft from inadvertent damage that may be caused by the screw threads 19. The cannulated sheath 1 is then removed by rotation with the aid of the thread-like ridge 5, and the guide pin is removed. A similar interference screw is driven into the tibia 10 by the same process to attach the opposite end of the graft.

In an alternate embodiment, the interference screw 16 is inserted in the cannula 13 of the sheath 1 before positioning the sheath between the graft 2 and the femur 14, such that the sheath 1 and the screw 16 are positioned between the graft 2 and the femur 14 simultaneously.

The present invention provides a tight interference fit between the graft bone block 6 and the femur 14 and between the graft bone block 4 and the tibia 10, enabling early mobilization and rapid healing. Still further, the attachment provided by the present invention has superior tensile and compressive strength as well as superior effective stiffness strength as compared to other ligament replacement procedures.

FIG. 8 illustrates the cannulated sheath with guide pin 36 extending therethrough. Sheath 1 preferably has a cannulation of approximately 8 mm. in diameter to accomodate screw 16. The inner diameter or cannulation 19 of the screw 16 is large enough to accommodate the guide pin 30.

Advantageously, in a preferred embodiment of the invention, guide pin 30 has a larger than normal diameter, preferably 2 mm. (conventional guide pins have a diameter of either 1 or 1.5 mm.). During insertion of the interference screw 16' between the bone block 6 and graft tunnel 8 as illustrated in FIG. 3, the screw may bite unevenly into the bone block 6 and the femur, causing it to tend to wander from the intended path set by the guide pin. Since guide pins are elongated, a thin diameter pin will not have sufficient strength to maintain the screw on course. Instead, as shown in FIG. 10, the end 9' of a typical thin guide pin 9 will bow as screw 16 "goes where it wants." By using a guide pin having an enlarged diameter (and an interference screw having a corresponding larger cannulation), screw insertion can be performed without guide pin arching, thereby providing greatly improved directional control of the screw.

Referring to FIG. 9, guide pin 30 includes laser etched markings 42, preferably spaced 25 mm. from each end of the pin (only one end of the pin being shown in FIG. 9). The etched marking 42 on the distal end 43 of the guide pin assist the surgeon in gauging when the pin has been inserted to the proper depth.

The previous example is for illustrative purposes only, as the present invention is not limited to any type of ligament replacement. Those skilled in the art can certainly contemplate a variety of different procedures in which the present invention can be advantageously applied. It is preferred, therefore, that the present invention be limited not by the specific disclosure herein, but only by the appended claims.

What is claimed is:

1. An apparatus for endosteal fixation of a substitute ligament graft by screw insertion, comprising:
   an interference screw having a front end and a back end, said back end having a semi-spherical shape and including means for preventing inadvertent damage to the graft comprising a rounded and smooth, unthreaded surface; and a removable cylindrical cannulated sheath for receiving said interference screw, said sheath having a proximal end and a distal end, said proximal end of said sheath having a cutout portion and a covered portion, said covered portion preventing threads of said interference screw from damaging said graft during screw insertion, and said cutout portion exposing a portion of said interference screw to permit said threads of said interference screw to cut into a bone tunnel wall during screw insertion.

2. An apparatus according to claim 1, wherein said front end of said interference screw is tapered.

3. An apparatus according to claim 1, wherein said rounded back end has an inverse hex-head for receiving a hex-head screwdriver.

4. An apparatus according to claim 1, wherein said interference screw is cannulated for receiving a guide pin.

5. An apparatus of claim 4, wherein said cannulation is sufficiently large to receive a guide pin having a diameter of 2 mm.

6. An apparatus according to claim 1, wherein said interference screw is made of titanium.

7. A method of endosteal fixation of a graft by screw insertion, comprising the steps of:
drilling a graft tunnel through adjacent first and second bone masses;
extending a graft attached between previously cut bone blocks under tension in said graft tunnel between said adjacent bone masses;
positioning a cannulated sheath between said graft and said first bone mass, said cannulated sheath having a cutout at one end, said sheath being positioned such that said graft is covered by said sheath and said first bone mass is exposed by said sheath;
inserting an interference screw in the cannula of said cannulated sheath, said interference screw having a rounded back end with a semi-spherical shape and a smooth, unthreaded surface;
driving said interference screw between said first bone mass exposed by said cutout and a corresponding one of said bone blocks; and
removing said cannulated sheath.

8. A method of endosteal fixation of a graft by screw insertion, comprising the steps of:
drilling a graft tunnel through adjacent first and second bone masses;
extending a graft attached between previously cut bone blocks under tension in said graft tunnel between said adjacent bone masses;
positioning a guide pin between said graft tunnel at said first bone mass and a corresponding one of said bone blocks;
placing a cannulated sheath over said guide pin, said guide pin guiding said sheath to a position between said graft and said first bone mass, said sheath having a cutout at one end, said sheath being positioned such that said graft is covered by said sheath and said first bone mass is exposed by said cutout;
placing a cannulated interference screw over said guide pin, said interference screw having a rounded back end with a semi-spherical shape and a smooth, unthreaded surface, said guide pin guiding said screw as it is inserted through the graft tunnel; and
driving said cannulated interference screw between said first bone mass and said corresponding bone block; and
removing said cannulated sheath.

9. A method according to claim 8, wherein said cannulated interference screw has an inverse hex-head for receiving a cannulated hex-head screwdriver, said cannulated interference screw being driven by said cannulated hex-head screwdriver.

10. An apparatus according to claim 1, wherein said interference screw has a cannulation sufficiently large to receive a guide pin having a diameter of approximately 2 mm.

* * * * *